United States Patent [19]

Jones et al.

[11] Patent Number: 4,560,821

[45] Date of Patent: * Dec. 24, 1985

[54] METHANE CONVERSION

[75] Inventors: C. Andrew Jones, Newtown Square; John J. Leonard, Springfield; John A. Sofranko, West Chester, all of Pa.

[73] Assignee: Atlantic Richfield Company, Los Angeles, Calif.

[*] Notice: The portion of the term of this patent subsequent to Apr. 17, 2001 has been disclaimed.

[21] Appl. No.: 522,938

[22] Filed: Aug. 12, 1983

Related U.S. Application Data

[63] Continuation-in-part of Ser. No. 412,650, Aug. 30, 1982, abandoned.

[51] Int. Cl.$^4$ .................................................. C07C 2/00
[52] U.S. Cl. ......................................... 585/500; 585/541; 585/654; 585/656; 585/661; 585/700; 585/741; 585/943; 585/415; 585/417; 585/418
[58] Field of Search ............... 585/500, 541, 700, 654, 585/658, 400, 413, 417, 418, 943, 661

[56] References Cited

U.S. PATENT DOCUMENTS

| | | | |
|---|---|---|---|
| 1,995,136 | 3/1935 | Winkler et al. | 585/500 |
| 2,216,130 | 10/1940 | Pier et al. | 585/943 |
| 2,326,799 | 8/1943 | Pier et al. | 585/700 |
| 2,608,534 | 8/1952 | Fleck | 585/654 |
| 3,900,525 | 8/1975 | Christman et al. | 585/541 |
| 4,066,704 | 1/1978 | Harris et al. | 585/658 |
| 4,205,194 | 5/1980 | Mitchell, III et al. | 585/500 |
| 4,239,658 | 12/1980 | Mitchell, III et al. | 585/500 |

FOREIGN PATENT DOCUMENTS 255829 5/1926 United Kingdom ............... 585/700

OTHER PUBLICATIONS

Keller, G. E., "Synthesis of Ethylene via Oxidative Coupling of Methane", J. of Catalysis, 73, 9–19 (1982).

*Primary Examiner*—William R. Dixon, Jr.
*Assistant Examiner*—Cynthia A. Prezlock
*Attorney, Agent, or Firm*—Craig E. Larson

[57] ABSTRACT

A continuous method for synthesizing hydrocarbons from a methane source which comprises contacting methane with particles comprising an oxidative synthesizing agent under synthesis conditions wherein particles recirculate between two physically separate zones: a methane contact zone and an oxygen contact zone. Preferably, particles are maintained in each of the two zones as fluidized beds of solids. Particularly effective oxidative synthesizing agents are reducible oxides of metals selected from the group consisting of Mn, Sn, In, Ge, Pb, Sb, and Bi.

43 Claims, No Drawings

METHANE CONVERSION

CROSS REFERENCED TO RELATED CASES

This application is a continuation-in-part of U.S. application Ser. No. 412,650, filed Aug. 30, 1982 now abandoned. This application is related to copending, concurrently filed U.S. patent application Ser. Nos. 522,925; 522,944; 522,942; 522,905; 522,877; 522,876; 522,906; and 522,935, the entire content of which are incorporated herein by reference.

BACKGROUND OF THE INVENTION

1. FIELD OF THE INVENTION

This invention relates to synthesis of hydrocarbons from a methane source. A particular application of this invention is a method for converting natural gas to more readily transportable material.

2. DESCRIPTION OF THE PRIOR ART

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example the methane content of natural gas may vary within the range of about 40 to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting, and revaporizing natural gas are complex, energy-intensive, and require extensive safety precautions. Transport of natural gas has been a continuing problem in the exploitation of natural gas resources. It would be extremely valuable to be able to convert methane (e.g., natural gas) to more easily handleable, or transportable, products. Moreover, direct conversion to olefins such as ethylene or propylene would be extremely valuable to the chemical industry.

In addition to its use as fuel, methane is used for the production of halogenated products (e.g., methyl chloride, methylene chloride, chloroform and carbon tetrachloride). Methane has also been used as a feedstock for producing acetylene by electric-arc or partial-oxidation processes. Electric-arc processes are operated commercially in Europe. In partial-oxidation processes, a feed mixture of oxygen and methane (the methane may contain other, additional hydrocarbons) are preheated to about 540° C. and ignited in a burner. Representative processes of this type are disclosed in U.S. Pat. Nos. 2,679,544; 3,234,300; and 3,244,765. Partial oxidation produces significant quantities of CO, $CO_2$ and $H_2$, yielding a dilute acetylene-containing gas and thereby making acetylene recovery difficult.

The largest, non-fuel use of methane is in the production of ammonia and methanol (and formaldehyde). The first, methane conversion, step of these processes is the production of a synthesis gas ($CO+H_2$) by reforming of methane in the presence of steam over, for example, a nickel catalyst. Typical reformers are tubular furnaces heated with natural gas, the temperature being maintained at 900° C. and the pressure at about 225 atmospheres.

Pyrolytic or dehydrogenative conversion of methane or natural gas to $C_2+$ hydrocarbons has previously been proposed. The conversion requires high temperatures (greater than about 1000° C.) and is characterized by the formation of by-product hydrogen. The patent literature contains a number of proposals to catalyze pyrolytic reactions, allowing conversion at lower temperatures. See, for example, U.S. Pat. Nos. 1,656,813; 1,687,890; 1,851,726; 1,863,212; 1,922,918; 1,945,960; 1,958,648; 1,986,238 and 1,988,873. U.S. Pat. No. 2,436,595 discloses and claims a catalytic, dehydrogenative methane-conversion process which employs fluidized beds of heterogeneous catalysts comprising an oxide or other compound of the metals of group VI or VIII.

Including oxygen in a methane feed for conversion over metal oxide catalysts has been proposed. Margolis, L. Ya., Adv. Catal. 14, 429 (1963) and Andtushkevich, T. V., et al, Kinet. Katal. 6, 860 (1965) studied oxygen/methane cofeed over different metal oxides. They report the formation of methanol, formaldehyde, carbon monoxide and carbon dioxide from methane/oxygen feeds. Higher hydrocarbons are either not formed or are converted much faster than methane.

SUMMARY OF THE INVENTION

The copending, concurrently-filed U.S. applications cross-referenced above disclose and claim methods for the synthesis of higher hydrocarbon products from methane wherein the inventions claimed relate primarily to the use of particular metal oxides as oxidative synthesizing agents and to the use of elevated pressures to promote formation of $C_3+$ hydrocarbon products.

The conversion of methane to higher hydrocarbons by contact with oxidative synthesizing agents involves multiple reactions which are not clearly understood. However, gas-(or vapor-) phase reaction products may be generally characterized as: (1) hydrocarbon products and (2) combustion products. Hydrocarbon products include alkanes, olefins and aromatics. The process is distinguished from pyrolytic methane conversion processes by the coproduction of water, rather than hydrogen, and by the competing combustion reactions occurring during methane contacting.

The presently claimed invention resides in the discovery that improved results (e.g., production of hydrocarbon products while reducing the formation of combustion products during methane-contacting) are obtained by employing a process wherein solids (i.e., solid particles) are continuously recirculated between two physically separate zones: a methane contact zone and an oxygen contact zone. Desirable product distributions may advantageously be obtained if particles comprising an oxidative synthesizing agent and a gas comprising methane are continuously introduced (e.g., at independently chosen feed rates) into the methane contact zone, which zone is maintained at selected contact temperatures. Moreover, maintaining fluidized beds of solids in the two contact zones enables control of average solids residence time in each zone and promotes mixing of the two-phase mixtures present in the zones. Average residence time of the methane containing feed is also controlled. This mode of operation further improves product distribution and reduces the formation of combustion products in the methane contact zone, especially when compared to cyclic processes involving intermittent or pulsed flow of methane and oxygen over solids maintained in a single contact zone or to processes wherein oxygen and methane are cofed over metal oxide catalysts.

Moreover, the process of the present invention provides the capability of producing a substantially uniform stream of desirable hydrocarbon products from relatively easily combustible material—methane—while employing oxidative synthesizing agents which are reduced during the methane-contacting. Such substantially uniform hydrocarbon product streams result in, for example, more effective and easier separation of products.

DETAILED DESCRIPTION OF THE INVENTION

Oxidative synthesizing agents are compositions comprising at least one oxide of at least one metal, which composition, when contacted with methane at a temperature selected within the range of about 500° to 1000° C., produces $C_{2}+$ hydrocarbon products, co-product water, and a composition comprising a reduced metal oxide. The composition thus contains at least one reducible oxide of at least one metal. The term "reducible" is used to identify those oxides of metals which are reduced by contact with methane at temperatures selected within the range of about 500° to 1000° C. The term "oxide(s) of metal(s)" includes (1) one or more metal oxides (i.e., compounds described by the general formula $M_xO_y$ wherein M is a metal and the subscripts $x$ and $y$ designate the relative atomic proportions of metal and oxygen in the compound) and/or (2) one or more oxygen-containing metal compounds, provided that such oxides and compounds have the capability of performing to produce higher hydrocarbon products as set forth herein.

Preferred oxidative synthesizing agents are disclosed in copending, concurrently-filed U.S. applications Ser. Nos. 522,925; 522,877; 522,876; and 522,906. Thus, preferred oxidative synthesizing agents comprise reducible oxides of metals selected from the group consisting of Mn,Sn,In,Ge,Sb,Pb, and Bi, and mixtures thereof. Particularly preferred oxidative synthesizing agents comprise a reducible oxide of manganese and mixtures of a reducible oxide of manganese with other oxidative synthesizing agents. More preferred are oxidative synthesizing agents which comprise $Mn_3O_4$.

In the present invention, reducible oxides are provided as solid particles. They may be supported by, or diluted with, a conventional support material such as silica, alumina, titania, zirconia, and the like, and combinations thereof. A presently preferred support is silica.

Supported solids (i.e., particles) can be prepared by any suitable method. Conventional methods such as adsorption, impregnation, precipitation, coprecipitation, or dry-mixing can be used. A suitable method is to impregnate the support with solutions of compounds of the desired metal. Some examples of suitable compounds are the acetate, acetylacetonate, oxide, carbide, carbonate, hydroxide, formate, oxalate, nitrate, phosphate, sulfate, sulfide, tartrate, fluoride, chloride, bromide or iodide. After impregnation, the preparation is dried in an oven to remove solvent and the dried solid is prepared for use by calcining, preferably in air at temperatures selected within the range of about 300° to 1200° C. Particular calcination temperatures will vary depending upon the particular metal compound.

Metal loadings on supported solids will generally be within the range of about 1 to 50 wt. % (calculated as the elemental metal(s) of the reducible oxides(s)).

The present process is distinguished from previously suggested methane conversion processes which rely primarily on interactions between methane and at least one of nickel and the noble metals, such as rhodium, palladium, silver, osmium, iridium, platinum and gold. An example of this type of process is disclosed in U.S. Pat. No. 4,205,194. The present process does not require that methane be contacted with one or more of nickel and such noble metals and compounds thereof.

Moreover, in a preferred embodiment, such contacting is carried out in the substantial absence of catalytically effective nickel and the noble metals and compounds thereof to minimize the deleterious catalytic effects of such metals and compounds thereof. For example, at the conditions, e.g., temperatures, useful for the methane contacting step of the present invention, these metals when contacted with methane tend to promote coke formation, and the metal oxides when contacted with methane tend to promote formation of combustion products $(CO_x)$ rather than the desired hydrocarbons. The term "catalytically effective" is used herein to identify that quantity of one or more of nickel and the noble metals and compounds thereof which when present substantially changes the distribution of products obtained in the contacting step of this invention relative to such contacting in the absence of such metals and compounds thereof.

In addition to methane, the feedstock employed in the method of this invention may contain other hydrocarbon or nonhydrocarbon components, although the methane content should be within the range of about 40 to 100 vol. %, preferably from about 80 to 100 vol. %, more preferably from about 90 to 100 vol. %.

Operating temperatures for the contacting of methane-containing gas and the particles comprising an oxidative synthesizing agent are selected from the range of about 500° to 1000° C., the particular temperature selected depending upon the metal oxides employed in the oxidative synthesizing agent. For example, all oxidative synthesizing agents have the capability of synthesizing higher hydrocarbons from a methane source when the temperature of the methane contact are selected within the lower part of the recited range. Reducible oxides of certain metals, however, may require operating temperatures below the upper part of the recited range to minimize sublimation or volatilization of the metals (or compounds thereof) during methane contact. Examples are: (1) reducible oxides of indium (operating temperatures will preferably not exceed about 850° C.); (2) reducible oxides of germanium (operating temperatures will preferably not exceed about 800° C.); and (3) reducible oxides of bismuth (operating temperatures will preferably not exceed about 850° C.).

Operating pressures for the methane contacting step are not critical to the presently claimed invention, but preferably are within the range of about 2–100 atmospheres, more preferably about 3–30 atmospheres. Use of elevated pressures to provide improved results, e.g., to promote formation of $C_3+$ hydrocarbon products is disclosed and claimed in copending, concurrently-filed U.S. application Ser. No. 522,935.

Contacting methane and an oxidative synthesizing agent to form higher hydrocarbons from methane also reduces the oxidative synthesizing agent and produces coproduct water. The exact nature of the reduced forms of oxidative synthesizing agents are unknown, and so are referred to herein as "reduced synthesizing agent" or as "a reduced metal oxide." Regeneration of a reducible metal oxide is readily accomplished by contacting reduced compositions with oxygen (e.g., an oxygen-containing gas such as air) at a temperature selected within the range of about 300° to 1200° C., the particular temperature selected depending on the metal(s) included in the oxidative synthesizing agent.

The methane contacting step and the oxygen contacting step are performed in physically separate zones with particles recirculating between the two zones. Thus, the present method for synthesizing hydrocarbons from a methane source comprises: (a) contacting in a first zone a gas comprising methane and particles comprising an oxidative synthesizing agent to form higher hydrocarbon products, coproduct water, and reduced synthesizing agent; (b) removing particles comprising reduced synthesizing agent from the first zone and contacting the reduced particles in a second zone with an oxygen-containing gas to form particles comprising an oxidative synthesizing agent; and (c) returning the particles produced in the second zone to the first zone.

Particles comprising an oxidative synthesizing agent which are contacted with methane may be maintained as fluidized, ebullating, or entrained beds of solids. Preferably, methane is contacted with a fluidized bed of solids.

Similarly, particles comprising reduced synthesizing agent which are contacted with oxygen may be maintained as fluidized, ebullating or entrained beds of solids. Preferably, oxygen is contacted with a fluidized bed of solids.

Thus in a presently preferred embodiment of the present invention, methane feedstock and particles comprising an oxidative synthesizing agent are continuously introduced into a methane contact zone maintained at synthesizing conditions. Synthesizing conditions include the temperatures and pressures described above. The methane feedstock is introduced at sufficient velocity such that the particles are fluidized. Gaseous reaction products from the methane contact zone (separated from any entrained solids) are further processed—e.g., they are passed through a fractionating system wherein the desired hydrocarbon products are separated from unconverted methane and combustion products. Unconverted methane is preferably recovered and recycled to the methane contact zone.

Of considerable importance to the process of this invention is the average residence time of particles in the methane contact zone. Selection of a desired solids residence time is dependent on the particular reducible metal oxide(s) incorporated in the particles comprising an oxidative synthesizing agent, the concentration of such active component, the feedrate and composition of the methane feedstock, and other operating conditions (esp. temperature and pressure of the contact zone). Preferably, the average residence time of particles in the fluidized bed contact zone is within the range of about 0.04 to 30 minutes, more preferably about 0.4 to 4 minutes. Optimum solids residence times for any particular oxidative synthesizing agent will decrease as methane contact temperatures, gas feed rates or hydrocarbon concentrations in the feed increase.

The feed rate of methane feedstock is related to the average residence time of particles, comprising an oxidative synthesizing agent, in the methane contact zone. Preferably, residence time of methane feedstock in the methane contact zone is within the range of about 0.1 to 100 seconds, more preferably about 1 to 20 seconds.

The size of particles comprising an oxidative synthesizing agent is preferably selected to render those particles capable of fluidization, preferably in a dense phase, in the methane contact zone. These particle sizes are usual and are not peculiar to this invention.

Particles comprising reduced synthesizing agent are contacted with molecular oxygen in an oxygen contact zone for a time sufficient to restore or maintain the activity of the agent by oxidizing at least a portion of the reduced metal oxide to produce a reducible oxide and by removing, i.e., combusting, at least a portion of any carbonaceous deposit which may form on the particles in the methane contact zone. The conditions of the oxygen contact zone will preferably include a temperature selected within the range of about 300° to 1200° C., pressures up to about 30 atmospheres, and average particle contact times within the range of about 3 to 120 minutes. Sufficient oxygen is preferably provided to oxidize all reduced metal oxide to produce a reducible oxide and to completely combust any carbonaceous deposit material deposited on the particles. At least a portion of the particles comprising an oxidative synthesizing agent, which are produced in the oxygen contact zone are returned to the methane contact zone.

The rate of solids withdrawal from the methane contact zone is desirably balanced with the rate of solids passing from the oxygen contact zone to the methane contact zone so as to maintain a substantially constant inventory of particles in the methane contact zone, thereby enabling steady state operation of the synthesis system.

What is claimed is:

1. In a method for converting methane to higher hydrocarbon products which comprises contacting a gas comprising methane at synthesizing conditions with at least one reducible oxide of at least one metal which oxides when contacted with methane at synthesizing conditions are reduced and produce higher hydrocarbon products and water, said contacting being carried out in the substantial absence of catalytically effective Ni, Rh, Pd, Ag, Os, Ir, Pt, Au and compounds thereof, the improvement which comprises:
   (a) continuously introducing and contacting the gas comprising methane and particles comprising said reducible metal oxides under synthesizing conditions in a first contact zone to form $C_2+$ hydrocarbons, coproduct water, and particles comprising a reduced metal oxide;
   (b) continuously removing particles comprising a reduced metal oxide from the first zone and contacting the particles with an oxygen-containing gas in a second zone to produce particles comprising a reducible metal oxide; and
   (c) returning particles formed in the second zone to the first zone.

2. A method for converting methane to higher hydrocarbon products which comprises:

(a) continuously introducing and contacting a gas comprising methane and particles comprising an oxidative synthesizing agent, which agent comprises at least one reducible oxide of at least one metal selected from the group consisting of Mn, Sn, In, Ge, Pb, Sb and Bi under synthesizing conditions in a first contact zone to form $C_{2+}$ hydrocarbons, coproduct water, and particles comprising reduced synthesizing agent, provided that when the metal selected is Mn or In, said contacting in the first zone is carried out in the substantial absence of catalytically effective Ni, Rh, Pd, Ag, Os, Ir, Pt, Au and compounds thereof;

(b) continuously removing particles comprising reduced synthesizing agent from the first zone and contacting the said reduced particles with an oxygen-containing gas in a second zone to produce particles comprising an oxidative synthesizing agent; and (c) returning particles formed in the second zone to the first zone.

3. The method of claim 2 wherein particles are maintained in the first zone as a fluidized bed of solids.

4. The method of claim 3 wherein particles are maintained in the second zone as a fluidized bed of solids.

5. The method of claim 2 wherein the average residence time of particles in the first zone is within the range of about 0.04 to 30 minutes.

6. The method of claim 3 wherein the average residence time of particles in the first zone is within the range of about 0.04 to 30 minutes.

7. The method of claim 2 wherein the average residence time of particles in the first zone is within the range of about 0.04 to 4 minutes.

8. The method of claim 3 wherein the average residence time of particles in the first zone is within the range of about 0.04 to 4 minutes.

9. The method of claim 2 wherein the residence time of methane feedstock in the first zone is within the range of about 0.1 to 100 seconds.

10. The method of claim 3 wherein the residence time of methane feedstock in the first zone is within the range of about 0.1 to 100 seconds.

11. The method of claim 2 wherein the residence time of methane feedstock in the first zone is within the range of about 1 to 20 seconds.

12. The method of claim 3 wherein the residence time of methane feedstock in the first zone is within the range of about 1 to 20 seconds.

13. The method of claim 2 wherein the temperature of the first zone is selected within the range of about 500° to 1000° C.

14. The method of claim 3 wherein the temperature of the first zone is selected within the range of about 500° to 1000° C.

15. The method of claim 2 wherein the gas comprising methane contains about 40 to 100 vol. % methane.

16. The method of claim 2 wherein the gas comprising methane contains about 80 to 100 vol % methane.

17. The method of claim 2 wherein the gas comprising methane contains about 90 to 100 vol % methane.

18. The method of claim 2 wherein a gas comprising methane is natural gas.

19. The method of claim 2 wherein a gas comprising methane is processed natural gas.

20. The method of claim 2 wherein a gas consisting essentially of methane is contacted with the said particles in the first zone.

21. The method of claim 2 wherein the said reducible oxide is associated with a support material.

22. The method of claim 21 wherein the support material is silica.

23. The method of claim 2 wherein the metal selected is Mn.

24. The method of claim 23 wherein the reducible oxide of Mn in $Mn_3O_4$.

25. The method of claim 2 wherein the metal selected is Sn.

26. The method of claim 25 wherein the reducible oxide of Sn is $SnO_2$.

27. The method of claim 2 wherein the metal selected is In.

28. The method of claim 27 wherein the reducible oxide of In is $In_2O_3$.

29. The method of claim 2 wherein the metal selected is Ge.

30. The method of claim 29 wherein the reducible oxide of Ge is $GeO_2$.

31. The method of claim 2 wherein the metal selected is Pb.

32. The method of claim 31 wherein the reducible oxide of Pb is PbO.

33. The method of claim 2 wherein the metal selected is Sb.

34. The method of claim 33 wherein the reducible oxide of Sb is $Sb_2O_3$.

35. The method of claim 2 wherein the metal selected is Bi.

36. The method of claim 35 wherein the reducible oxide of Bi is $Bi_2O_3$.

37. The method of claim 23 wherein the temperature of the first zone is within the range of about 500° to 1000° C.

38. The method of claim 25 wherein the temperature of the first zone is within the range of about 500° to 1000° C.

39. The method of claim 31 wherein the temperature of the first zone is within the range of about 500° to 1000° C.

40. The method of claim 33 wherein the temperature of the first zone is within the range of about 500° to 1000° C.

41. The method of claim 27 wherein the temperature of the first zone is within the range of about 500° to 850° C.

42. The method of claim 35 wherein the temperature of the first zone is within the range of about 500° to 850° C.

43. The method of claim 29 wherein the temperature of the first zone is within the range of about 500° to 800° C.

* * * * *